(12) United States Patent
Dierkes et al.

(10) Patent No.: US 8,636,512 B2
(45) Date of Patent: Jan. 28, 2014

(54) SET OF ELEMENTS FOR PRODUCING A DENTAL PROSTHESIS, SYSTEM FOR PRODUCING A DENTAL PROSTHESIS OR A SET OF ELEMENTS, AND CORRESPONDING PRODUCTION METHODS

(75) Inventors: Stephan Dierkes, Bremen (DE); Jan Eilers, Verden (DE); Ole Hinrichs, Bremen (DE); Wolfgang Stolzner, Ganderkesee (DE); Bernardo Franco, Bremen (DE); Carsten Vagt, Oyten (DE)

(73) Assignee: Bego Bremer Goldschlagerei Wilh. Herbst GmbH & Co. KG, Bremen (DE)

( * ) Notice: Subject to any disclaimer, the term of this patent is extended or adjusted under 35 U.S.C. 154(b) by 586 days.

(21) Appl. No.: 12/374,298

(22) PCT Filed: May 16, 2007

(86) PCT No.: PCT/EP2007/054736
§ 371 (c)(1),
(2), (4) Date: Apr. 7, 2009

(87) PCT Pub. No.: WO2008/009495
PCT Pub. Date: Jan. 24, 2008

(65) Prior Publication Data
US 2010/0015572 A1    Jan. 21, 2010

(30) Foreign Application Priority Data

Jul. 19, 2006  (DE) .......................... 10 2006 033 794

(51) Int. Cl.
*A61C 8/00*  (2006.01)
*B29C 33/40* (2006.01)
*A61C 9/00*  (2006.01)

(52) U.S. Cl.
USPC ................... 433/201.1; 433/202.1; 433/212.1

(58) Field of Classification Search
USPC .............. 425/110, 111, 113, 117, 129.1, 175;
249/54, 62; 433/201.1, 202.1, 212.1
See application file for complete search history.

(56) References Cited

U.S. PATENT DOCUMENTS 5,092,022 A * 3/1992 Duret ........................... 29/896.1
6,667,112 B2 * 12/2003 Prasad et al. .................. 428/552

(Continued)

FOREIGN PATENT DOCUMENTS

EP    1293174 A1    3/2003
EP    1661529 A2    5/2006

(Continued)

OTHER PUBLICATIONS

International Searching Authority-Europe, Notification of Transmittal of the International Search Report and Written Opinion of the International Searching Authority, PCT/EP2007/054736, dated Sep. 12, 2007, 8 pages.

*Primary Examiner* — Atul P. Khare
(74) *Attorney, Agent, or Firm* — Sunstein Kann Murphy & Timbers LLP

(57) ABSTRACT

A set of elements is described for use in the production of a dental prosthesis (20), in particular of a crown, a bridge, an inlay or an onlay, comprising:
  a framework (3) and
  one or more model parts (5) for defining parts of the outer contour of a veneer (15) for the framework (3),
wherein the model part or parts (5) can be mounted on the framework (3) in such a way that, at one and the same time,
(i) a gap (7) remains between the model part or parts (5) and the framework (3) and
(ii) the model part or parts (5) define parts [lacuna] the outer contour.
Corresponding methods and systems are also described.

11 Claims, 3 Drawing Sheets

(56) References Cited

U.S. PATENT DOCUMENTS

| | | |
|---|---|---|
| 6,848,898 B2 * | 2/2005 | Shoher et al. .............. 425/405.1 |
| 7,236,842 B2 * | 6/2007 | Kopelman et al. .............. 700/98 |
| 2003/0123943 A1 * | 7/2003 | Hamada .......................... 409/96 |
| 2005/0177266 A1 * | 8/2005 | Kopelman et al. ............ 700/117 |
| 2005/0186540 A1 * | 8/2005 | Taub et al. .................... 433/223 |
| 2006/0115793 A1 * | 6/2006 | Kopelman et al. ............ 433/215 |
| 2006/0115795 A1 * | 6/2006 | Marshall et al. .............. 433/218 |
| 2006/0122719 A1 * | 6/2006 | Kopelman et al. .............. 700/98 |
| 2006/0261503 A1 * | 11/2006 | Sago et al. ....................... 264/16 |
| 2009/0026643 A1 * | 1/2009 | Wiest et al. ...................... 264/16 |
| 2009/0095629 A1 * | 4/2009 | Wiest et al. ................... 204/471 |

FOREIGN PATENT DOCUMENTS

| | | |
|---|---|---|
| WO | WO 02076327 A1 | 10/2002 |
| WO | WO 03017864 A1 | 3/2003 |
| WO | WO 2005007009 A1 * | 1/2005 |
| WO | WO 2005046502 A1 * | 5/2005 |

* cited by examiner

SET OF ELEMENTS FOR PRODUCING A DENTAL PROSTHESIS, SYSTEM FOR PRODUCING A DENTAL PROSTHESIS OR A SET OF ELEMENTS, AND CORRESPONDING PRODUCTION METHODS

The present invention relates to a set of elements (set of parts) for use in the production of a dental prosthesis, in particular of a crown, a bridge, an inlay or an onlay. The invention also relates to methods for producing a corresponding dental prosthesis comprising a framework and a veneer and also to a system for producing a dental prosthesis of a set of elements according to the invention. Finally, the invention relates also to a method for producing a set of elements according to the invention.

A dental prosthesis, for example a crown, can be used to restore, replace or replicate a tooth that has been damaged or destroyed. A number of different options are available regarding the material from which the prosthesis is made.

In functional terms, (part or all of) a tooth can be adequately restored or replaced by a metal prosthesis. For aesthetic reasons, however, there is in many cases a reluctance to make a dental prosthesis entirely from metal.

The use of glass ceramics to make prostheses is on the increase, for reasons both of aesthetics (translucency) and above all of biocompatibility. This material is known as a press ceramic because the production process involves pressing the molten glass into a mold. Color gradations can be obtained on this prosthesis by subsequently painting it with a brush. Owing to its low strength, however, the field of application of this type of full ceramic is restricted to crowns and anterior dental bridges with a maximum of three units.

The best aesthetic results are obtained, however, by providing a ceramic or metal framework with a layered veneer. This veneer is applied to at least part of the framework. The framework determines the main mechanical properties such as strength and flexural strength, whilst the optical properties and the general surface properties of the dental prosthesis are established by the veneer. Plastics material or ceramic are generally used as materials for the veneer. Veneering ceramics are in many cases preferred over veneering plastics materials, since only the excellent mechanical and physical values of ceramics such as hardness and strength permit a long-term use.

When using veneering ceramics it is important to match the coefficients of thermal expansion (CTE) of the framework material and of the veneering material. If the coefficients differ too greatly, stress can occur. This can lead to separation of the or [lacuna] to cracks in the veneer.

In many cases the veneering material is applied by hand to the framework, using a brush for example. This veneering method involves coating a ceramic or metal framework with layers of a dentine core compound, a transparent compound and an incisal compound, for example. An opaquing compound is additionally also applied to the metal framework in advance. The application of these layers and the associated firing processes are time-consuming, and depending on the skill and dexterity of the operator, the quality of the results may vary.

DE 27 05 770 A1 proposes the use of electrophoresis to apply a veneering ceramic to a metal framework. Electrophoretic deposition allows only uniform layers to be created, however. It does not allow for a creative influencing of the outer contour (other than the coating thickness). Manual finishing is therefore unavoidable. Furthermore, this method is only suitable for metal frameworks, since the surface to be coated must be electrically conductive.

Methods for producing veneered metal and ceramic crowns are known from U.S. Pat. No. 5,092,022. The crown is produced from matching defined components (framework and veneer), the outer contour of the framework and the inner contour of the veneer being defined in a standardized manner and only the inner contour of the framework and the outer contour of the veneer being adapted to the intended application by means of subtractive shaping. Alternatively, the framework is built first and the inner contour of the veneer is machined to match the outer contour of the framework before the two are assembled. U.S. Pat. No. 5,092,022 also proposes producing a framework in the desired shape together with an outer mold reproducing the outer contour of the veneer, combining the framework and outer mold to make a casting mold and casting a plastics material veneer directly onto the framework.

Standardized, defined molds can often be adapted only with difficulty to the specific conditions of an individual case. If the framework and veneer are adapted to one another by machining, as in U.S. Pat. No. 5,092,022, the production tolerances must be very small, and this is only possible with a correspondingly large amount of effort. Furthermore, the casting mold according to U.S. Pat. No. 5,092,022 consists of at least two components, as a result of which casting defects occur, especially at the contact surfaces between the mold parts, which defects require increased finishing.

Manually modeling a wax model of a veneering ceramic structure, embedding the model together with the framework, then burning out the wax model and filling the mold that is created with a ceramic, for example with a press ceramic, in order to produce the prosthesis, is known (see G. G. J Dröge: "Die Metallgerüst-Konstruktion für das Heißpressverfahren" das dental-labor, No. 3/1977, G. G. J. Dröge: "Die Porzellan-Press-Technik (I)", das dental-labor, No. 4/1969 and E. R. McPhee: "Heißpressverfahren bei der Porzellan/Metall-Aufbrenntechnik", das dental-labor, No. 10/1976).

This method, which is known as the "lost wax" method, is used according to DE 199 29 441 A1, for example, for producing fully anatomically modeled crowns or partly anatomically modeled frameworks.

A method is known from EP 0 033 492 A1 for producing a wax casting model for a primary part of a telescopic crown in which the contour of the casting model is calculated on the basis of stored geometric data for a tooth stump and subtractively shaped.

WO 03/017864 A1 teaches a method for producing a solid cast metal prosthesis, in which the geometric data for a set of teeth are used to produce by automated means a prototype of the prosthesis to be molded, which prototype serves to create a casting mold for the entire prosthesis using the lost wax method.

The methods known from EP 0 033 492 A1 and WO 03/017864 A1 can only be used to produce a one-piece prosthesis from a single material and not, however, a dental prosthesis comprising a framework and a veneer.

A method for producing a dental prosthesis comprising a framework and a veneer is known from DE 199 22 870 A1. In this case the manual application of veneering material is replaced by a computer-aided, automated application using coating nozzles. This method requires a complex equipment construction, however, and so its use makes little sense in practice.

According to EP 1 543 797 A1, and similarly to the teaching of U.S. Pat. No. 5,092,022, a mold provided for press-molding veneering material is created by milling or grinding, on the basis of a set of geometric data for the prosthesis to be created. The mold holds the framework to be veneered, and the veneering ceramic is injected into the remaining cavity to fill it.

WO 2005/046502 A1 describes a system and an arrangement for producing dental prosthesis parts. Described in particular is a method in which a wax mold is embedded into an embedding compound and then burned out. Porcelain material is then pressed into the resulting negative mold under vacuum and at high temperatures. The method described in WO 2005/046502 produces a dental crown consisting of two layers, wherein a first layer is made of porcelain material and represents the outer mold of the dental crown and wherein a second layer is made of a different material and forms a cap, the inner surface of which corresponds to the outer face of a tooth stump, for example.

A body, which is made of a wax mixture or a corresponding plastics material which can be melted out and/or burned without residue, for producing a casting model of a tooth crown is known from DE 81 20 687. This body is pre-shaped and is adapted in the oral cavity to the respective dental situation. In order to reduce the amount of material used, the distance between an inner wall of the body and the stump is determined by way of considerations resulting from the stressing of the body. According to DE 81 20 687, a noble metal tooth crown is produced with the body as the casting model. During mounting of the crown the gap between the crown and the stump is filled with cement.

It was the object of the present invention to disclose sets of elements for use in the production of a dental prosthesis, methods for producing a dental prosthesis and also systems for producing a dental prosthesis or a set of elements according to the invention, allowing in a simple manner the production of a dental prosthesis comprising a framework and a veneer. The invention is intended in this case to be applicable also to frameworks which have undercuts and/or are provided with an opaque layer.

According to a first aspect of the present invention, the object set is achieved by a set of elements (i.e. a set of parts), for use in the production of a dental prosthesis, in particular of a crown, a bridge, an inlay or an onlay, comprising:
 a framework and
 one or more model parts for defining (generally main) parts of the outer contour of a veneer for the framework,
wherein the model part or parts can be mounted on the framework in such a way that, at one and the same time,
(i) a gap remains between the model part or parts and the framework and
(ii) the model part or parts define parts of the outer contour (generally main parts of the outer contour).

The framework has in this case regularly an inner mold corresponding with a high degree of precision to the outer mold of a treatment situation (for example of a tooth stump). The one or more model parts define (more or less completely and more or less precisely) the outer contour of the dental prosthesis, but are in some cases processed further, for example using subtractive shaping methods. According to the invention, it is sufficient if the model part or parts roughly define the outer contour of the dental prosthesis and (see below in this regard) precise adaptation is carried out in later method steps to the requirements of the oral situation. Preferably, the model part or parts define at least the chewing surface or parts thereof and also parts of the side faces of the veneer.

A set of elements according to the invention is designed in such a way that the model part or parts can be mounted on the framework. The inner mold of the model part or parts is however in this case selected in such a way that a gap remains between the model part or parts and the framework if the model part or parts are mounted on the framework in such a way that they define the outer contour of the dental prosthesis. This constitutes a significant difference between the set of elements according to the invention and previously known sets of prosthesis components in which a framework is contacted, without the provision of a gap, with a model part which defines the outer contour of the veneer.

Preferably, the gap between the model part or parts and the framework is configured in such a way that in the arrangement in which the model part or parts are mounted on the framework and the model part or parts define the outer contour, there is at all points a spacing between the model part or parts and the framework, so that said model part or parts and said framework do not at any point touch one another.

Preferably, in a set of elements according to the invention, the framework and the model part or the plurality of model parts are configured in such a way that between them a gap having a thickness of at least 0.05 mm is present, at least in certain portions, if the model part or parts define the outer contour of the dental prosthesis in the intended manner. Preferred gap widths lie in the range of from 0.05 to 3, preferably 0.1 to 1.5 mm.

The thickness of the model part or parts lies preferably in the range of from 0.2 to 1.5 mm, particularly preferably in the range of from 0.3 to 0.9 mm. It is greatly preferable to select the thickness of the model part or parts so as to be substantially constant; in some cases the thickness of the model or models can however also vary, for example in order to allow the protuberances to protrude from the lens or to embody a model part so as to taper in the direction of the preparation edge. However, in such cases too, the thickness range of between 0.2 and 1.5 mm is preferably at no point departed from. Exceptions are however possible.

The framework of a set of elements according to the invention comprises or consists preferably of metal, a metal alloy, a glass ceramic or ceramic material and thus has a high melting point of preferably >1,000° C. The model part or parts of a set of elements according to the invention are preferably meltable or combustible at a temperature at which the framework is stable, i.e. does not melt, burn, shrink or buckle. During heating, the framework can however be reversibly altered in accordance with its coefficient of thermal expansion.

Preferably, the model part or parts are made of wax and/or plastics material; preference is generally given to materials which can burn at temperatures of ≤1,000° C., preferably ≤900° C., for a holding time of 1 h, down to a residual ash content of ≤0.25% by weight, preferably down to a residual ash content of ≤0.05% by weight.

Preferably, a set of elements according to the invention comprises an adhesive for (at least partly) filling out the gap and for fixing the model part or parts on the framework. An adhesive of this type should in this case also be meltable or combustible at a temperature at which the framework is stable. In the assembled state an adhesive layer is thus located on the framework and one or more model parts, which define the outer contour of a veneer, are located on the adhesive layer. The adhesive fills out (at least partly) a gap between the framework and the model part or parts and fixes the model part or parts on the framework. The adhesive and the model part or parts jointly form the model of a veneer, wherein the outer contour is defined (at least partly) by the model part or parts and the inner contour of the veneer is defined by the adhesive (at the interface to the framework). The term "adhesive" includes in the present case also adhesives which comprise fillers and have an adhesive effect with respect to the framework and model part or model parts. Preferably, the adhesive also burns at temperatures of ≤1,000° C., preferably ≤900° C., for a holding time of 1 h, down to a residual ash content of ≤0.25% by weight, preferably ≤0.05% by weight.

Preferably, the adhesive is a compound which is viscous at 25° C. and is curable preferably within a few minutes, for example on irradiation with light, by heating, drying or by means of a chemical reaction. Furthermore, use may also be made of adhesives which are free-flowing at an elevated temperature—preferably a processing temperature of between 30 and 100° C.—and cure on cooling.

A set of elements according to the invention can comprise, in addition to the elements mentioned hereinbefore, also further elements which can in particular be selected from the group consisting of: material for producing a model of a casting channel; molding material (for example a conventional commercial embedding compound); mixing liquid for a molding material; veneering material (in particular ceramic veneering material for use as a press ceramic in a hot pressing method, for example in the form of press ceramic pellets or veneering ceramic cylinders); adhesive; modeling material (for example wax), for example for the subsequent application of material to the model or for creating the edge seal between the prosthesis and the preparation limit, glazing compound, stains, opaques, press stamp.

In so far as the set of elements comprises a separate material for producing a model of a casting channel, this material is preferably also meltable or combustible at a temperature at which the framework is stable. The preferred combustibility criteria, which have been mentioned with regard to the model parts and the adhesive, preferably apply.

Preference is given to a set of elements according to the invention in which the framework comprises or consists of a metal, a metal alloy (noble metal-free or noble metal-containing), a glass ceramic and/or a ceramic material. Metals and metal alloys are well suited, owing to their mechanical properties, for functionally replacing a tooth or a tooth part. Functionally tooth-like properties can also be attained using suitable glass ceramics and ceramics. As a result of the use of the suitable materials for the framework, the mechanical properties of the entire prosthesis can be extensively defined.

Depending on the requirements of the individual case, it is advantageous if in a set of elements according to the invention the framework has (a) an anatomically reduced shape (with generally varying thickness) or (b) an at least substantially constant thickness. An anatomically reduced shape is in this case present if the outer form of the framework resembles the outer form of the finished dental prosthesis, wherein the framework conventionally has varying thicknesses. Cf. in this regard also the description of preferred configurations hereinafter.

If the framework of a set of elements according to the invention has one or more undercuts and/or is the framework of a bridge, two or more model parts, which jointly define the outer contour of the veneer for the framework and preferably are precisely adapted to one another, are advantageously provided in a set of elements according to the invention. The provision of two or more model parts is however not required in all cases, for example even if use is made of a framework comprising one or more undercuts; on the contrary, in some cases all that is required is to provide a sufficiently wide gap between the framework (comprising undercuts) and model parts or a model which is shortened in length. In the latter case supplementary modeling of the veneer, which is not defined by the model part, can be carried out for example using wax.

Further preferred configurations of a set of elements according to the invention will emerge from the subsequent description of methods and systems according to the invention, the appended figures, as well as the description of the figures, and the appended claims.

The present invention relates also to a method for producing a dental prosthesis comprising a framework and a veneer, in particular of a crown, a bridge, an inlay or an onlay, including the following steps:

producing or providing a set of elements according to the invention as described hereinbefore (in particular in one of the configurations which are specified as being preferred), mounting the model part or parts on the framework, so that (i) a gap remains between the model part or parts and the framework and, at one and the same time,
(ii) the model part or parts define the outer contour and if appropriate a casting channel, fixing the model part or parts on the framework by means of the or an adhesive (the adhesive is conventionally already applied to the framework and/or on the inside to the model before the model is mounted on the framework; excess adhesive is in this case pressed out from the gap between the framework and model part(s)), forming a negative mold of a veneer for the framework by enclosing adhesive and the model part or model parts between the framework and a molding material and subsequently removing adhesive and the model part or model parts and filling the negative mold with veneering material for producing the dental prosthesis.

With regard to the method according to the invention, that which was stated hereinbefore with regard to preferred sets of elements according to the invention applies accordingly.

The method according to the invention, such as it has been described hereinbefore, seeks to produce or to provide a set of elements according to the invention. The framework and/or the model part or parts for defining the outer contour of a veneer for the framework of a set of elements of this type can in this case be produced by additive and/or subtractive shaping. The shaping of the framework and/or of the model part or parts is in this case carried out preferably by means of computer-aided production, preferably in each case by means of a rapid prototyping method. Preferably, production methods such as milling (in particular if ceramic material is used) or laser sintering (in each case preferably as a rapid prototyping method) are used for producing the framework. Additive methods, such as 3D printing or stereolithography, or subtractive method, such as milling (in each case preferably as a rapid prototyping method), are preferably used for producing the model part or parts.

The additive and/or subtractive shaping of the framework and/or model part(s), which is carried out preferably by means of computer-aided production and particularly preferably by means of a rapid prototyping method, is preferably carried out in each case on the basis of predetermined three-dimensional geometric data. The three-dimensional geometric data are in this case predetermined in that the oral situation, a wax-up and/or an impression of the oral situation are scanned and the three-dimensional geometric data are predetermined in a computer-aided manner on the basis of the scan data thus obtained and also if appropriate of additional user inputs. In so far as an impression of the oral situation is scanned, the counter bite is preferably also scanned. Additional user inputs can for example be carried out by a dental technician, wherein for example the scan data set is manipulated by additional user inputs. Thus, the dental technician can for example set contact points in which the dental prosthesis is intended to touch neighboring teeth. On the basis of the scan data, which is if appropriate manipulated by additional user inputs, a proposal is preferably computed for the overall geometry of the veneered unit and also the partial geometries of the framework and the model part or model parts which for example a dental technician can continue to alter in a computer-aided manner by means of drawing functions provided. On the basis of the data obtained or generated as described hereinbefore, the assemblability of the framework and model part or parts is then calculated or ensured, preferably in a computer-aided manner. In the event of discrepancies, this is displayed for example on a computer monitor and/or corrections are carried out automatically on the three-dimensional geometric data for the framework and/or the model part or parts. In addition the program calculates, preferably automatically, the volume of the veneer to be created and specifies for example the required mass for press ceramic cylinders to be used (with regard to the use of press ceramic, see below).

The mounting of the model part or parts on the framework is carried out in a method according to the invention in such a way that (i) a gap (conventionally filled with adhesive) remains between the model part or parts and the framework and, at one and the same time, (ii) the model part or parts define the outer contour (of a dental prosthesis to be produced). The mounting of the model part or parts on the framework is carried out in this case preferably in an articulator; in so far as use is made primarily of frameworks which are substantially metallic, an opaque is preferably applied to said frameworks beforehand (the resulting framework then comprises for example a metal alloy and an opaque ceramic material). During production of a dental bridge or crown it may be necessary for two or more model parts to be mounted on a framework. This is for example frequently the case if undercuts rule out or impede the use of an individual model part. It is advisable, before the mounting of the model part or parts, first to mount the framework on a master model (for example of a tooth stump). In addition it is advisable to apply, even before the mounting of the model part or parts on the framework, adhesive to the inside of the model part or parts and/or the outside of the framework. Based on the counter bite and the neighboring teeth, it is easy to orient in the articulator the model part or parts into the desired position in which they define the outer contour. Excess parts of the model part or parts can if necessary be removed, for example by milling. In so far as it is desirable, additional model part compound can be applied, even after the mounting of the model part or parts, to the model part or parts in order locally to increase the model part thickness. In so far as adhesive was applied to the model part or parts and/or the framework even before the mounting, gaps or flaws, which are already present during mounting, between the preparation limit (on the master model) and the framework and also between the preparation limit and the model part or parts can be filled up with the adhesive; the adhesive then cures in the gap between the model part or parts and the framework and fixes the model part or parts and the framework relative to one another. Excess adhesive can be pressed out, in proximity to the preparation limit between the model/models and framework or between the model/models and master model, from the gap. It is thus possible to ensure that the prosthesis to be created has a good edge seal relative to the preparation limit. The excess adhesive can subsequently be removed. Alternatively, use may be made of an amount of adhesive that is not sufficient more than to fill up the gap between the model/models and framework, so that no edge seal of the prosthesis relative to the preparation limit is created. In this case the edge seal is conventionally filled up by subsequent application of adhesive or another curable compound.

Within the scope of the method according to the invention, a respective casting channel is applied, conventionally separately, to the model part or parts for each unit which is to be veneered (caps and intermediate bridge members each constitute a unit) and is made of a material which can be burned out (such as for example wax or plastics material).

The framework thus prepared (comprising the framework itself, one or more model parts and also adhesive and if appropriate a separate casting channel) is subsequently embedded into a molding material, so that adhesive and the model part or model parts (and also conventionally a separately introduced casting channel) are enclosed between the framework and the molding material. This method step is carried out conventionally using a muffle. During preheating of the muffle (which can be carried out in the conventional manner in a preheating furnace), the model part or parts are removed, preferably melted out or burned out, together with the adhesive (including if appropriate fillers which are present). A negative mold (hollow mold) of a veneer, which is delimited by the framework and the molding material, is thus formed in a manner known per se. The negative mold is then filled, preferably by means of a hot pressing method, with veneering material for producing the veneered dental prosthesis. Preferably, a press ceramic in the plastic state is pressed into the negative mold at temperatures of between 700° C. and 1,100° C. Subsequently, the overpressed framework (consisting of the framework and press ceramic pressed thereon) is freed from the embedding compound and the sprue (press ceramic material in the casting channel) is separated off. Individual coloring and characterization can be carried out by means of conventional painting processes. Conventionally, in a last working step, glazing compound is blended in a gel-like consistency and applied in a sufficiently thick layer. Fissures and the crown edge region can be excluded from these last method steps. As a result of the application of glazing compound, the surface of the restoration is sealed, imparting thereto an attractive and natural gloss.

In particular if the dental prosthesis is a bridge and/or the framework has one or more undercuts, two or more model parts are preferably used in a method according to the invention.

In a method according to the invention the molding material which is used is preferably a refractory material, particularly preferably an (in particular conventional commercial) embedding compound. The technical parameters of the embedding compound are preferably adapted to those of the framework and to those of the veneer.

Particular preference is given to a method according to the invention for producing a dental prosthesis including the following steps:

producing a set of elements according to the invention (preferably in a configuration specified above as being preferable), wherein the framework which is present in the set of elements and/or the model part or parts present therein are produced in a computer-aided manner by additive and/or subtractive shaping on the basis of predetermined three-dimensional geometric data, mounting, preferably by means of an articulator, the model part or parts on the framework, so that (i) a gap remains between the model part or parts and the framework and, at one and the same time, (ii) the model part or parts define the outer contour and if appropriate a casting channel, fixing the model part or parts on the framework by means of the or a adhesive (with regard to the conventional procedure, see above), forming a negative mold (hollow mold) of a veneer for the framework by enclosing adhesive and the model part or model parts between the framework and a molding material and subsequently removing adhesive and the model part or model parts by melting-out and/or burning-out and filling the negative mold with veneering material by means of a hot pressing method for producing the dental prosthesis.

Methods according to the invention (and accordingly also sets of elements according to the invention) have over known methods the advantage that the model part or parts do not rest directly against the framework. As a result, method induced inaccuracies in the creating of the framework and the model part or parts have in practice no, or no significant, effect. If for example an opaque layer is to be applied to a metal (basic) framework, the layer thickness thereof cannot be determined precisely in advance. However, since according to the invention a gap is provided between the framework (including the opaque layer) and the model part or parts, this impossibility of determining the layer thickness in advance does not have an adverse effect.

In a method according to the invention for producing a dental prosthesis the model part or parts end preferably at a distance of from 0 to 3 mm, preferably 0.5 to 3 mm before the preparation limit (which may be seen for example on the master model on which the framework is preferably mounted in the method according to the invention). In a further preferred variant the model part or the model parts end at the level of the equator of the prosthesis. This alternative may for example be preferable if marked differences do not allow the mounting of a one-part model, but additional model parts are not desirable. In the case of both preferred methods the non-modeled part of the veneer is conventionally filled up with a corresponding material (for example wax).

The present invention relates also to a system for producing a dental prosthesis or a set of elements according to the invention (as described above, preferably in a configuration characterized above as being particularly preferred). According to the invention a system of this type comprises a predetermining means for predetermining three-dimensional geometric data for a framework and one or more model parts for defining parts of the outer contour of a veneer for the framework and if appropriate of a casting channel, wherein the model part or parts can be mounted on the framework in such a way that, at one and the same time, (i) a gap remains between the model part or parts and the framework and (ii) the model part or parts define parts of the outer contour, preferably main parts of the outer contour, a framework producing means for producing the framework on the basis of the three-dimensional geometric data and a model part producing means for producing the model part or parts on the basis of the three-dimensional geometric data.

The predetermining means present in a system according to the invention operate preferably in a computer-aided manner.

The framework producing means provided in a system according to the invention and/or the model part producing means provided are configured, in a system according to the invention, preferably for computer-aided additive and/or subtractive shaping. In this case the shaping is carried out preferably by means of a rapid prototyping method.

Preferably, a system according to the invention comprises, in addition to the system components mentioned hereinbefore, scan means for scanning an oral situation, a corresponding wax-up of the prosthesis and/or an impression of an oral situation and for generating corresponding scan data, wherein the predetermining means interacts with the scan means and is configured for predetermining in a computer-aided manner the three-dimensional geometric data on the basis of the scan data and if appropriate of additional user inputs.

It will be understood that all of the components of the system according to the invention are intended and suitable preferably for carrying out corresponding method steps such as are specified hereinbefore and hereinafter in detail.

A system according to the invention preferably further comprises:

negative mold forming means for forming a negative mold of a veneer for the produced framework by enclosing adhesive and the produced model part or produced model parts between the framework and a molding material and subsequently removing adhesive and the model part or model parts and/or filling means for filling the or a produced negative mold of a veneer for the produced framework with veneering material for producing the dental prosthesis.

Particularly suitable as negative mold forming means are the conventional materials and tools for producing negative molds, i.e. for example molding compounds (in particular embedding compounds), mixing liquids, muffles, etc. Furthermore the term "negative mold forming means" also includes heating means (for example preheating furnaces) or the like which can be used for removing adhesive, sprue channel(s) and the model part or model parts.

Examples of filling means include in particular—as mentioned hereinbefore with regard to the method according to the invention—veneering materials, in particular press ceramics.

These press ceramics have preferably a cylindrical shape.

The method according to the invention for producing a dental prosthesis includes in a first step producing or providing a set of elements according to the invention. The present invention accordingly relates also to a method for producing a set of elements according to the invention, wherein a set of elements of this type is intended in particular to be applicable for use in a method according to the invention for producing a dental prosthesis. Such a method according to the invention for producing a set of elements includes the following steps:

scanning the oral situation, a corresponding wax-up of the prosthesis and/or an impression of an oral situation and generating corresponding scan data, determining three-dimensional geometric data in a computer-aided manner starting from (a) the scan data and if appropriate (b) additional user inputs, computer-aided additive and/or subtractive shaping of the framework and/or of the model part or parts, preferably by means of a rapid prototyping method, on the basis of the predetermined three-dimensional geometric data.

It will be understood that in a method according to the invention for producing a set of elements according to the invention use is preferably made of scan means and/or predetermining means and/or framework producing means and/or model part producing means such as have been described hereinbefore with regard to a system according to the invention. It will also be understood that the method according to the invention can be used for producing a set of elements as a first method part within the scope of a more extensive method according to the invention for producing a dental prosthesis. The carrying-out of the previously defined method steps (scanning the oral situation; determining three-dimensional geometric data in a computer-aided manner; computer-aided shaping of the framework and/or of the model part or parts) is followed, in a method configured in this manner for producing a dental prosthesis, by the "mounting", "fixing", "forming a negative mold" and also "filling the negative mold" steps described in detail hereinbefore.

Preferably, in a method according to the invention for producing a set of elements a system according to the invention is provided and used for determining the three-dimensional geometric data in a computer-aided manner and for computer-aided additive and/or subtractive shaping of the framework and/or of the model part or parts and if appropriate for scanning the oral situation, a corresponding wax-up of the prosthesis and/or the impression of an oral situation and for generating corresponding scan data.

Further aspects of the present invention will emerge from the subsequent description of the figures and from the appended claims.

The invention will be described hereinafter in greater detail with reference to the appended figures, in which.

Figure 1:
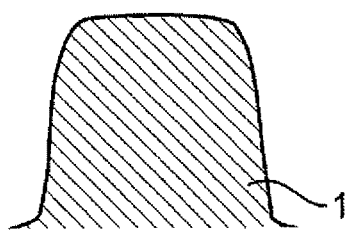
FIG. 1 shows the model 1 of a tooth stump.
Figure 2:
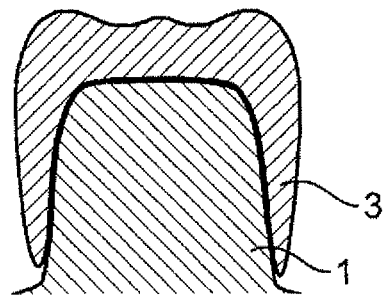
FIG. 2 shows the framework 3 which is mounted on the model 1 according to FIG. 1.
Figure 3A:
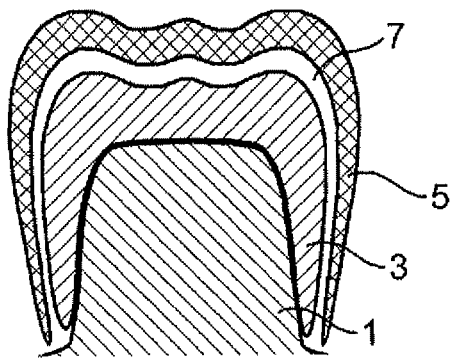
FIG. 3a shows the framework 3 according to FIG. 2 and also the associated model part 5.
Figure 4:
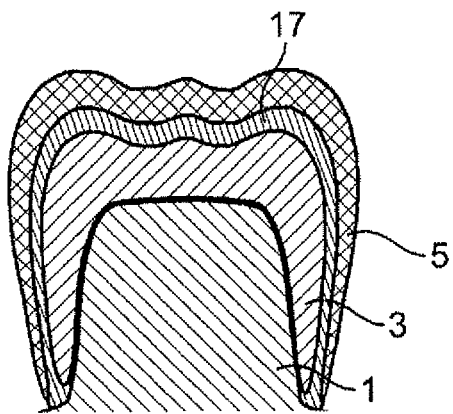
Figure 5:
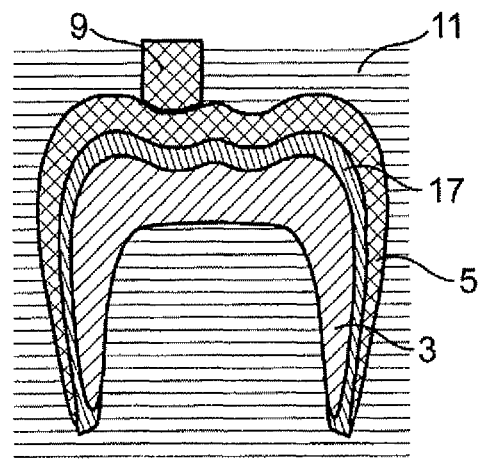
Figure 6:
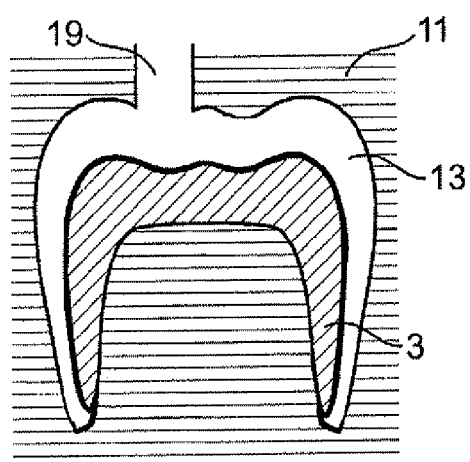
Figure 7:
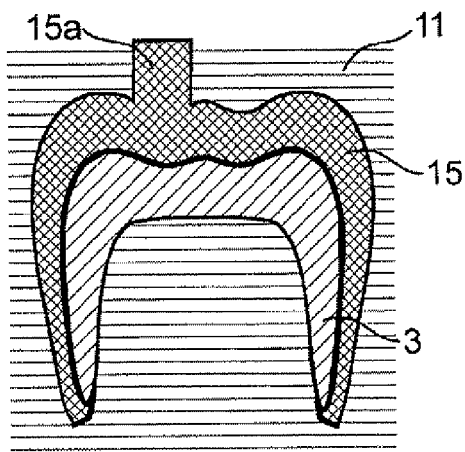
Figure 8:
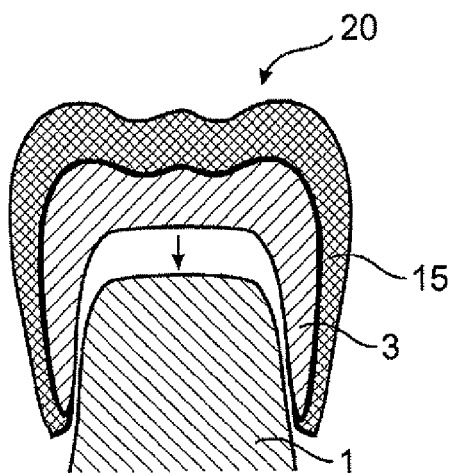
Figure 9:
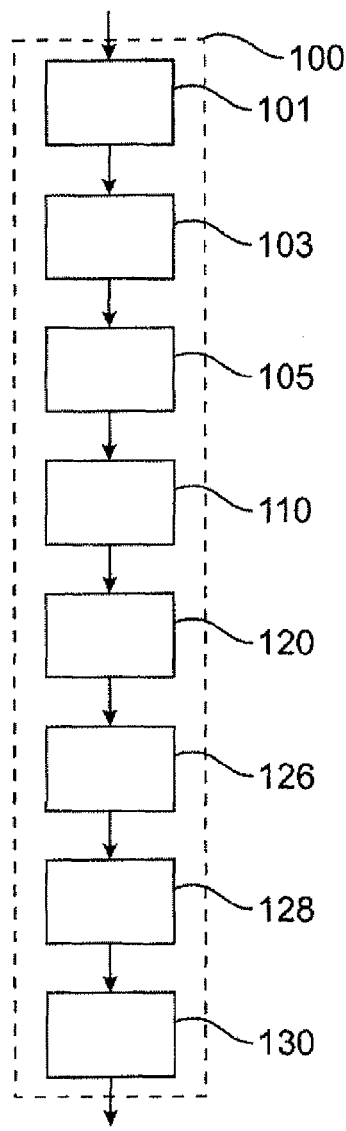
Figure 10:
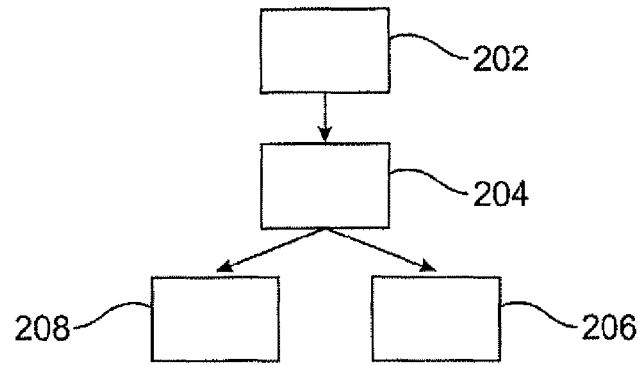
Figure 11:
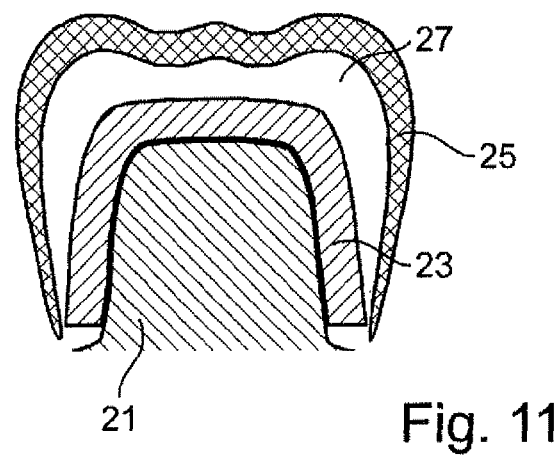
Figure 12:
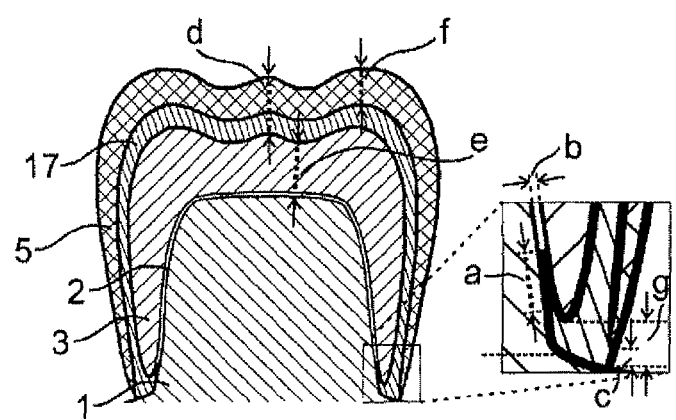

FIG. 4 shows the framework 3 and model part 5 according to FIG. 3a with adhesive 17 arranged in a gap-filling manner;

FIG. 5 shows the arrangement according to FIG. 4 with the additionally attached casting channel 19, embedded in the embedding compound 11;

FIG. 6 shows the negative mold 13 enclosed between the embedding compound 11 and the framework 3 from FIG. 2;

FIG. 7 shows the arrangement according to FIG. 6, although in this case the negative mold 13 is filled with veneering material 15;

FIG. 8 shows the dental prosthesis 20 which is made up of the framework 3 and veneer 15 and mounted on the model 1 according to FIG. 1;

FIG. 9 is a flow chart of a first embodiment of a method according to the invention for producing a dental prosthesis;

FIG. 10 is a flow chart of a first embodiment of a method according to the invention for producing a set of elements which is suitable for use in a method according to the invention, in particular for use in a method according to FIG. 9;

FIG. 11 shows an arrangement similar to 3a, but with a framework 23 of approximately constant thickness; and FIG. 12 shows an arrangement similar to FIG. 4, illustrating the parameters of the three-dimensional geometric data.

FIG. 1 shows a model 1 of a tooth stump. Of particular importance are in this case the geometric data for the outer contour of the model 1, to which the inner contour of the framework 3 (see FIG. 2) is adapted.

FIG. 2 shows the model 1 of a tooth stump according to FIG. 1 and a framework 3 which is arranged thereon and has an inner contour adapted to the outer contour of the model 1 (see FIG. 1). The lower edge of the framework 3 ends 1-2.5 mm before the preparation limit of the model 1 (and accordingly to the actual tooth stump) in the direction of the jaw.

Such "vertical reduction" is preferable for aesthetic reasons and allows the formation of a ceramic shoulder. The framework 3 has an anatomically reduced shape, i.e. the thickness of the framework 3 is not constant and its form already resembles that of the striven-for dental prosthesis 20 (cf. FIG. 8); obviously, the framework 3 is however smaller than the striven-for dental prosthesis 20.

FIG. 3a shows the framework 3 with a model part 5 mounted thereon by means of an articulator. The model part 5 defines main parts of the outer contour of a veneer 15 of the framework 3, but not the inner contour of the veneer 15. The framework 3 and model part 5 were created on the basis of scan data which were obtained by scanning the oral situation, a wax-up of the prosthesis and/or an impression of the oral situation (including the counter bite). If appropriate, additional user inputs were taken into account.

Figure 3B:
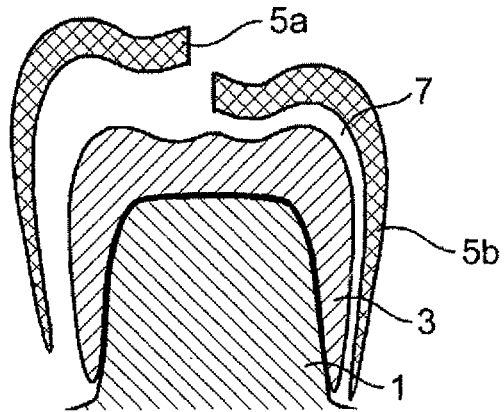
FIG. 3b shows the framework 3 according to FIG. 2 and also two associated model parts 5a, 5b.

A gap 7, which is intended for receiving viscous adhesive 17, is located between the model part 5 and the framework 3. The model part 5 is made of a wax material or plastics material which can be burned (in a preheating furnace) substantially without residue. The model part 5 can also be mounted on the framework 3, although the framework 3 tapers somewhat downward and a certain undercut is thus present. This is possible since the model part 5 has a certain flexibility and the dimensions of the gap width are sufficiently large. Alternatively, use may be made of two or more model parts 5 which jointly define the outer contour of the veneer 15. A configuration of this type is shown in FIG. 3b.

FIG. 4 shows the framework 3 and the model part 5 in the arrangement according to FIG. 3a. However, the gap 7, which is still present in the arrangement according to FIG. 3a, is filled out in the arrangement according to FIG. 4 by an adhesive 17 which fixes the model part 5 on the framework 3. The adhesive 17 and model part 5 jointly form the model 5 of a veneer 15 for the framework 3.

FIG. 5 shows the arrangement according to FIG. 4, wherein the model 9 of a casting channel 19 is additionally arranged on the model part 5. The arrangement illustrated in FIG. 5 is embedded into an embedding compound 11.

FIG. 6 shows the embedding, illustrated in FIG. 5, of the framework 3 in an embedding compound 11 wherein the model part 5 and adhesive 17 and also the model 9 of the casting channel 19 are removed (for example by burning-out in a preheating furnace). Instead of said elements there is a negative mold 13 (hollow mold) of the veneer 15, which can be filled via a casting channel 19.

The view in FIG. 7 corresponds to the view from FIG. 6, wherein the negative mold 13 of the veneer 15 is filled with veneering material (press ceramic) 15. The casting channel 19 also contains veneering material 15a.

FIG. 8 shows the finished dental prosthesis 20 with the framework 3 and the veneer 15, which matches the model of the tooth stump 1 and also (taking into account the necessity of a cement gap 2 the corresponding tooth stump (not shown). The veneering material 15a in the region of the casting channel was removed beforehand from the veneer 15.

FIG. 9 shows in a flow chart at first embodiment of a method according to the invention for producing a dental prosthesis. A first step 101 of the method 100 provides a set of elements according to the invention, comprising a framework and also one or more model parts for defining the outer contour of a veneer for the framework, wherein the model part or parts can be mounted on the framework in such a way that, at one and the same time, (i) a gap remains between the model part or parts and the framework and (ii) the model part or parts define the outer contour and if appropriate the casting channel.

In a second step 103 adhesive is applied to the inside of the model part or parts and/or to the framework.

In a further step 105 the model part or parts are mounted on the framework in such a way that
(i) a gap (filled at least partly with adhesive) remains between the model part or parts and the framework and, at one and the same time,
(ii) the model part or parts define the outer contour and if appropriate a casting channel. Preferably, the mounting of the model part or parts on the framework is carried out using an articulator. The adhesive fixes the model part or parts on the framework. Excess adhesive is pressed out from the gap in proximity to the preparation limit and removed.

Cf. in this regard in particular FIGS. 3a, 3b and 4.

In a separate follow-up step 110 a casting channel (a plurality of casting channels in the case of a plurality of units to be veneered) is mounted on the model part or the model parts.

Subsequently, in a step 120 the arrangement made up of the framework, adhesive, model part or model parts and also casting channel is embedded into a molding material (embedding compound), cf. in particular FIG. 5.

Subsequently, in a step 126 the adhesive and the model part or the model parts are removed, for example burned out by heat treatment. This produces a negative mold between the framework and embedding compound. Cf. in this regard in particular FIG. 6.

In a follow-up step 128 the negative mold is filled with veneering material for producing the dental prosthesis, preferably by means of a hot pressing method. Cf. in this regard in particular FIG. 7.

The method of hot pressing a ceramic into a suitable shape is known to a person skilled in the art, so that this method will not be examined in greater detail. A method and a corresponding furnace for producing tooth replacement parts by the hot pressing method is described for example in EP 0 231 773 A1. An application of this method for producing a full ceramic dental structure with a zirconium oxide pin as the framework is proposed in DE 196 30 412 A1. A development of the method from EP 0 231 773 A1 may be inferred from DE 101 36 584 A1.

In an additional step 130 the produced dental prosthesis is mounted (after separating-off of the casting channel) for sample purposes on the master model or on the tooth stump or the tooth stumps and attended to as required (the term "attending to" includes in this case adapting the framework and/or the prosthesis to the tooth stump, usually by milling and grinding). Cf. in this regard in particular FIG. 8.

FIG. 10 shows in a flow chart a first embodiment of a method according to the invention for producing a set of elements, which is suitable for use in a method according to the invention for producing a dental prosthesis, in particular for use in a method according to FIG. 9.

In a first step 202 a scan means is used to scan an oral situation, a wax-up and/or an impression of an oral situation (including the counter bite) and to generate corresponding scan data. In a follow-up step 204 a predetermining means is used to predetermine in a computer-aided manner three-dimensional geometric data of the framework to be produced and of the model part or parts to be produced for defining the outer contour of a veneer for the framework. The framework and the model part or parts, the three-dimensional geometric data of which are to be predetermined, are in this case to be configured in such a way that the model part or parts can be mounted on the framework in such a way that, at one and the same time, (i) a gap remains between the model part or parts and the framework and (ii) the model part or parts define parts of the outer contour. In addition the computer-aided determining of the three-dimensional geometric data in step 204 can take into account additional user inputs which the user can carry out on the predetermining means or using an input means (for example a computer keyboard) which interacts with the predetermining means.

In a follow-up step 206 a framework producing means is used to produce, on the basis of the three-dimensional geometric data, the framework which precisely matches, for example with its inner contour, the model of a tooth stump. Cf. in this regard in particular FIG. 2. The framework producing means is in this case configured preferably for additive and/or subtractive shaping and in particular for carrying out a rapid prototyping method. Preferably, the framework is thus produced (shaped) by means of a rapid prototyping method.

In a step 208, which can be carried out at the same time as or in a time-offset manner relative to step 206, a model part producing means is used in the method according to FIG. 10 to produce the model part or parts which define the outer contour of a subsequent veneer and can be mounted on the framework, so that a gap remains. The model part producing means is preferably configured in turn (and just like the framework producing means) for computer-aided additive and/or subtractive shaping. Preferably, the model part producing means allows a rapid prototyping method to be carried out.

Particularly preferably, ceramic or metal material is used in step 206 for producing the framework and this material is milled or laser-sintered.

Preferably, wax or plastics material is used in step 208 for producing the model part or parts and the model parts are produced therefrom by means of an additive computer-aided method such as 3D printing or stereolithography or by means of a subtractive computer-aided method such as milling.

Preferably, the scan means used in step 202 interacts with the predetermining means used in step 204, wherein the predetermining means is configured for predetermining in a computer-aided manner the three-dimensional geometric data on the basis of the scan data and if appropriate of additional user inputs.

The elements (the framework and also the model part or model parts) produced in steps 206 and 208 can be provided in particular in step 101 of the method according to FIG. 9 and thus serve for producing a dental prosthesis.

The scan means can be configured in such a way as to allow (i) optical recording directly in the patient's mouth (including for example by means of X-rays) or on a model of the set of teeth or (ii) direct or indirect mechanical recording (scanning). Other scan methods are however also possible.

FIG. 11 shows the arrangement of a framework 23 having a substantially constant thickness on the model 21 of a tooth stump. A model part 25 is mounted on the framework 23. A gap 27 is located between the model part 25 and framework 23. The arrangement according to FIG. 11 corresponds to the arrangement according to FIG. 3a, although FIG. 11 shows, instead of an anatomically reduced framework, a framework 3 having a substantially constant thickness. It will be understood that the present invention also allows the use of frameworks 3 which can neither be described as being anatomically reduced nor have a substantially constant thickness.

FIG. 12 shows the arrangement according to FIG. 4, a cement gap 2 between the framework 3 and the model 1 of the tooth stump (or the real tooth stump) also being shown. The cement gap 2 allows the adhering/cementing of the dental prosthesis 20 to the tooth stump. Also illustrated are parameters of the three-dimensional geometric data, based on which the framework 3 and the model part or parts 5 are created; the illustrated positions of parameters determined are in this case to some extent merely exemplary.

a Length of the region of the framework 3 abutting directly, i.e. without a cement gap 2, against the model 1 of the tooth stump. This region begins at the lower edge of the framework 3. a lies in the range of from 0 to 2 mm, preferably in the range of from 0.1 to 0.5 mm.
b Thickness of the cement gap 2
c Distance of the model part or parts 5 from the preparation limit (vertical reduction of the model part or parts 5). c lies preferably in the range of from 0 to 3 mm.
d Measure for the anatomical reduction of the framework 3
e Thickness of the framework 3
f Thickness of the model part or parts 5
g Measure for the vertical reduction of the framework 3

The arrangement according to FIG. 12 shows an anatomically reduced framework 3. It will be understood that frameworks having a substantially constant thickness e or non-anatomically reduced frameworks having a variable thickness e may also be used. In such a case the parameter d describes the distance between the framework and the outer contour of a veneer for the framework 3.

The invention claimed is:

1. A set of dental elements for use in the production of a dental prosthesis, the set of elements comprising:
   a framework forming an inner portion of the dental prosthesis and configured to be mounted on a tooth stump; and
   one or more model parts mounted on the framework in such a way that a gap remains between the model part or parts and the framework, the gap configured to receive an adhesive to fix the model part or parts on the framework, and the model part or parts defining parts of the outer contour of a veneer for the framework.

2. The set of elements as claimed in claim 1, wherein the model part or parts are meltable or combustible at a temperature at which the framework is stable.

3. The set of elements as claimed in claim 1, wherein the model part or parts are made of wax and/or plastics material.

4. The set of elements as claimed in claim 1, wherein the gap is configured to be at least partly filled with the adhesive to fix the model part or parts on the framework.

5. The set of elements as claimed in claim 4, wherein the adhesive is meltable or combustible at a temperature at which the framework is stable.

6. The set of elements as claimed in claim 1, further comprising one or more elements selected from the group consisting of:
   a material for producing a model of a casting channel,
   a molding material,
   a mixing liquid,
   a veneering material,
   a glazing compound,
   a stain,
   an opaque,
   a modeling material, and
   a press stamp.

7. The set of elements as claimed in claim 1, further comprising a material for producing a model of a casting channel that is meltable or combustible at a temperature at which the framework is stable.

8. The set of elements as claimed in claim 1, wherein the framework comprises a metal, a metal alloy, a glass ceramic and/or a ceramic material.

9. The set of elements as claimed in claim 1, wherein the framework has (a) an anatomically reduced shape with varying thickness or (b) an at least substantially constant thickness.

10. The set of elements as claimed in claim 1, wherein:
    the framework has one or more undercuts and/or is the framework of a bridge, and
    two or more model parts are provided.

11. The set of elements as claimed in claim 1, wherein the dental prosthesis is a crown, a bridge, an inlay, or an onlay.

* * * * *

UNITED STATES PATENT AND TRADEMARK OFFICE
CERTIFICATE OF CORRECTION

PATENT NO. : 8,636,512 B2  
APPLICATION NO. : 12/374298  
DATED : January 28, 2014  
INVENTOR(S) : Stephan Dierkes et al.

Page 1 of 1

It is certified that error appears in the above-identified patent and that said Letters Patent is hereby corrected as shown below:

On the title page of the patent:

(30) Foreign Application Priority Data

Change 10 2006 033 794  
    To 10 2006 033 794.8

Signed and Sealed this  
Seventeenth Day of June, 2014

Michelle K. Lee  
*Deputy Director of the United States Patent and Trademark Office*

UNITED STATES PATENT AND TRADEMARK OFFICE
CERTIFICATE OF CORRECTION

PATENT NO. : 8,636,512 B2
APPLICATION NO. : 12/374298
DATED : January 28, 2014
INVENTOR(S) : Dierkes et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 788 days.

Signed and Sealed this
Twenty-second Day of September, 2015

Michelle K. Lee
*Director of the United States Patent and Trademark Office*